(12) United States Patent
Gamboa Burgos

(10) Patent No.: US 11,794,961 B2
(45) Date of Patent: Oct. 24, 2023

(54) LIQUID DISPENSING DEVICE COMPRISING DROP-CHECK MECHANISM, AIR FILTER AND MULTIFUNCTION MEMBRANE VALVE

(71) Applicant: Alejandro Gamboa Burgos, Lima (PE)

(72) Inventor: Alejandro Gamboa Burgos, Lima (PE)

( * ) Notice: Subject to any disclaimer, the term of this patent is extended or adjusted under 35 U.S.C. 154(b) by 0 days.

(21) Appl. No.: 17/597,336

(22) PCT Filed: Jul. 1, 2020

(86) PCT No.: PCT/PE2020/050008
§ 371 (c)(1),
(2) Date: Jan. 3, 2022

(87) PCT Pub. No.: WO2022/005310
PCT Pub. Date: Jan. 6, 2022

(65) Prior Publication Data
US 2022/0315296 A1    Oct. 6, 2022

(51) Int. Cl.
| | | |
|---|---|---|
| *B65D 47/18* | (2006.01) | |
| *B65D 47/20* | (2006.01) | |
| *B65D 47/32* | (2006.01) | |
| *B05B 11/04* | (2006.01) | |
| *B05B 11/00* | (2023.01) | |
| *A61F 9/00* | (2006.01) | |
| *A61J 1/05* | (2006.01) | |

(52) U.S. Cl.
CPC ............... *B65D 47/32* (2013.01); *A61F 9/00* (2013.01); *A61J 1/05* (2013.01); *B05B 11/0044* (2018.08); *B05B 11/04* (2013.01); *B05B 11/047* (2013.01); *B65D 47/18* (2013.01); *B65D 47/20* (2013.01)

(58) Field of Classification Search
CPC ........ B65D 47/32; B65D 47/18; B65D 47/20; B05B 11/04; B05B 11/0044; B05B 11/047; A61F 9/00; A61J 1/05
See application file for complete search history.

(56) References Cited

U.S. PATENT DOCUMENTS

| | | | | |
|---|---|---|---|---|
| 4,699,300 | A * | 10/1987 | Blake ................. | B65D 47/2081 222/481 |
| 5,154,325 | A * | 10/1992 | Ryder .................. | B05B 11/047 222/215 |
| 7,303,098 | B2 * | 12/2007 | Backes ................. | B65D 47/18 222/212 |
| 8,454,828 | B2 * | 6/2013 | Wochele ............. | B05B 11/1016 222/189.09 |
| 8,827,124 | B2 * | 9/2014 | Painchaud ......... | B65D 47/2087 222/189.06 |
| 9,402,765 | B2 * | 8/2016 | Chibret ................ | B65D 47/18 |
| 10,640,268 | B2 * | 5/2020 | Painchaud ........... | A61J 1/1425 |

(Continued)

*Primary Examiner* — Frederick C Nicolas
(74) *Attorney, Agent, or Firm* — Pearson IP; Loren Donald Pearson

(57) ABSTRACT

A liquid dispensing device includes a multifunction membrane valve that, in addition to allowing the dispensing of drops with a drop-check mechanism, ensures and isolates the passage of the air to be filtered so that it does not contaminate the liquid in the interior of the dispensing device; it has a reduced number of parts; it facilitates proper assembly by counter pressure, without the need for threads or complex coupling elements; it avoids the need for rotational alignment when assembling the parts, among other advantages.

8 Claims, 10 Drawing Sheets

(56) References Cited

U.S. PATENT DOCUMENTS

2015/0150719 A1* 6/2015 Chibret ................ A61F 9/0008
                                                      604/295
2019/0185227 A1* 6/2019 Painchaud ............. B65D 47/18

* cited by examiner

LIQUID DISPENSING DEVICE COMPRISING DROP-CHECK MECHANISM, AIR FILTER AND MULTIFUNCTION MEMBRANE VALVE

FIELD OF THE INVENTION

The present invention falls within the technical field of ophthalmic product dispensers, disclosing specifically a multi-dose drop dispensing device comprising a drop-check mechanism, an air filter for preservative-free use and a multifunction membrane valve.

DESCRIPTION OF THE RELATED ART

In the state of the art there are some technologies related to multi-dose droppers without preservatives, with drop-check mechanisms and a system of air purification, examples of this type of technology are found in patent documents U.S. Pat. No. 9,345,616B2 or U.S. Pat. No. 9,238,532B2 from the company Nemera la Verpilliere SAS or document U.S. Pat. No. 9,833,356B2 from the company Aptar Radolfzell GmbH, which involve spring valves or membrane valves.

However, these antecedents have the great disadvantage that their manufacture involves the coupling of a large number of pieces of very complex dimensions which do not allow their processing under a concept of using simple and fast manufacturing technologies (for example, through the conventional Blow/fill/seal technology), also they have the disadvantage that their peaks are flattened and thick, which does not allow an easy and precise guidance when applying eye-drops by the user.

Another disadvantage of these devices is that the filter itself for the purification of the air entering the system is wide, thick or of a large diameter with respect to the diameter of the mouth of the bottle. None of the technologies of the state of the art allow assembly in a single operation, nor do they specify a solution to the problem of assembling the parts without the need for rotational alignment so that the flow of compensation air enters seamlessly inside the device. Additionally, the dispensing devices of the state of the art do not comprise a protection cap with sufficient extension to raise and protect the air extract hole of the upper casing.

Likewise, through the patent application PCT/PE2020/050003, protection has been claimed for a liquid dispenser with a drop-check mechanism and an air filter, that has a concept of simple and fast manufacturing technologies, which presents an elongated beak, allows assembly without the need for rotational alignment so that a flow of compensation air enters seamlessly into the device. However, this antecedent requires individual sealing rings that are manufactured with double shot and multi-material plastic injection, which implies an increase in the number of parts manufactured with this technology, makes it more complex and presents the risk that the rings can be misaligned by the pressure exerted.

SUMMARY OF THE INVENTION

The present invention solves the aforementioned technical problems through the proposal of a liquid dispensing device comprising a membrane valve with an upper part substantially cylindrical or conical, which covers the surface of the valve holder and also a lower part that extends along part of the external surface of the flow circulation body. This membrane valve has multiple functions, such as, allowing the regulated flow of the liquid through its elongated area and its opening for dispensing liquids, allowing the proper sealing and isolation of the area for entrance of the air to be filtered by the system, as well as ensuring the fit of the flow circulation body with the upper casing. This elongated membrane valve has, in its lower area, a diameter portion along its width or horizontal extension and continuously a vertically extending portion; wherein the vertical extension portion comprises windows for the flow of air into the bottle, preferably, these windows are interspersed at the same height (within an annular distribution).

The vertical extension portion comprises at least one annular protrusion in its lower end zone that allows the securing between the upper casing and the flow circulation body. An annular depression may be provided in the upper casing at the same height as the annular protrusion of the vertical extension portion of the membrane valve, such that protrusion and depression fit together.

The horizontal extension portion or diameter extension comprises at least one annular protrusion on its inner surface which is suitable for engaging with an annular depression in the upper part of the flow circulation body.

Considering the characteristics mentioned above, the present invention with respect to its predecessor makes it possible to obviate the use of the upper and lower sealing rings as individual pieces.

Some additional components of the invention are described below:

An annular depression in the flow circulation body is disposed at the height of the membrane valve windows, in such a way that a free annular space is created between the upper casing and the membrane valve. Optionally, another annular space can be arranged, at the same level, between the other side of the membrane valve and the flow circulation body. These annular spaces avoid the need to align by rotating the parts at assembly time.

The flow circulation body includes at least one through hole for air compensation at the level of the windows of the membrane valve. The air that enters by this compensation through hole is filtered and/or purified through a filter, this filter is preferably fixed by pressure or by fitting to an internal zone of the flow circulation body; once the air has been filtered and/or purified it is suitable for having contact with the liquid inside the dispenser, via this compensating through hole the air is conducted to compensate the exit of the dispensed liquid (when using the present device). The upper part of the circulation body has an annular depression in order to fit into the annular protrusion of the horizontal portion of the membrane valve; there are upper liquid through holes in the upper surface of the circulation body, by which the liquid first passes through these holes into the dispenser when the bottle is pressed; the seat or valve holder is in the form of a bar or elongated portion with channels along its length and is positioned on the upper surface of the flow circulation body. In this way, the compensation air to be filtered by the system enters and circulates between the protrusions, preferably annular, located between the windows of the membrane valve; furthermore, the protrusion of the horizontal portion of the membrane valve has the function of preventing leakages of the liquid when the bottle is pressed and the liquid circulates through the body. This protrusion of the horizontal portion of the valve also serves to exert a counter pressure and allows a suitable assembly, that is, it works as a "spring" mechanism that allows the assembly to be hooked up by pressure against at least two elements at the time of assembly.

The membrane valve or valve body comprises a droplet-forming opening located coincidentally with the tip of the valve holder. When the bottle is pressed, the pressure causes the liquid in the bottle to circulate between the valve holder and the membrane valve; and, when the bottle is released, the space between the valve holder and the membrane valve closes. In another preferred form, this membrane valve has an upper termination that tapers, leaving a small open space (a space between 1 mm and 1.8 mm in diameter, preferably 1.4 mm) and is followed by internal ends that widen in the shape of an inverted cone for droplet formation.

Another element of the present invention is the upper casing or beak that covers the membrane valve and part of the flow circulation body, where the lower part of the upper casing has a pressure coupling with the lower end of the flow circulation body, and the upper casing comprises at least one side hole disposed at the height of the windows of the membrane valve; and, another element is a lid with a central protrusion to displace residual drops and evaporate them through at least one evaporation window located on the upper part or upper side of the lid, a snap on or threaded coupling element could be provided on the external face of the upper housing for coupling with the neck of a drop bottle.

The present invention manages to integrate a set of relevant technical characteristics in a single device, providing the following technical effects:

It avoids the use of individual insulating and securing rings, which leads to a reduction of components to be manufactured, thus reducing the use of double-shot and multi-material technologies in an injection machine with the ability to inject liquid silicone (LSR); likewise, the way in which the elements have been designed allows the quick and easy coupling of the pieces through protrusions or hooking up notches and pressure mechanisms, eliminating the need for threads.

It has a reduced number of parts, compared to the antecedents of the state of the art, which require the assembly of several complex components to achieve the objective of providing a dispenser for multi-drop bottles comprising an air filtering mechanism with a drop-check system and free of preservatives.

It does not require rotation alignment of the flow circulation body with the upper casing or the membrane valve to create a communication path for allowing free air into the system, nor is required a rotational alignment of the membrane valve with respect to the other elements—it is merely enough with the direct press-fit assembly, one over the other.

The present invention has the same dimensions as a bottle for dispensing ophthalmic liquids which uses traditional Tip & Cap technology. Thus, its manufacturing dimensions meet the requirements to function correctly in blowing/filling/sealing machines (blow/fill/seal) with a standard tip and cap insertion system (Tip & Cap Insertion System) and without any modification, thus allowing their mass production and cost reduction.

BRIEF DESCRIPTION OF THE DRAWING

The following figures illustrate some embodiments of the present invention—said figures or their description are not intended to limit in any way the scope of protection defined by the claims.

Figure 1:
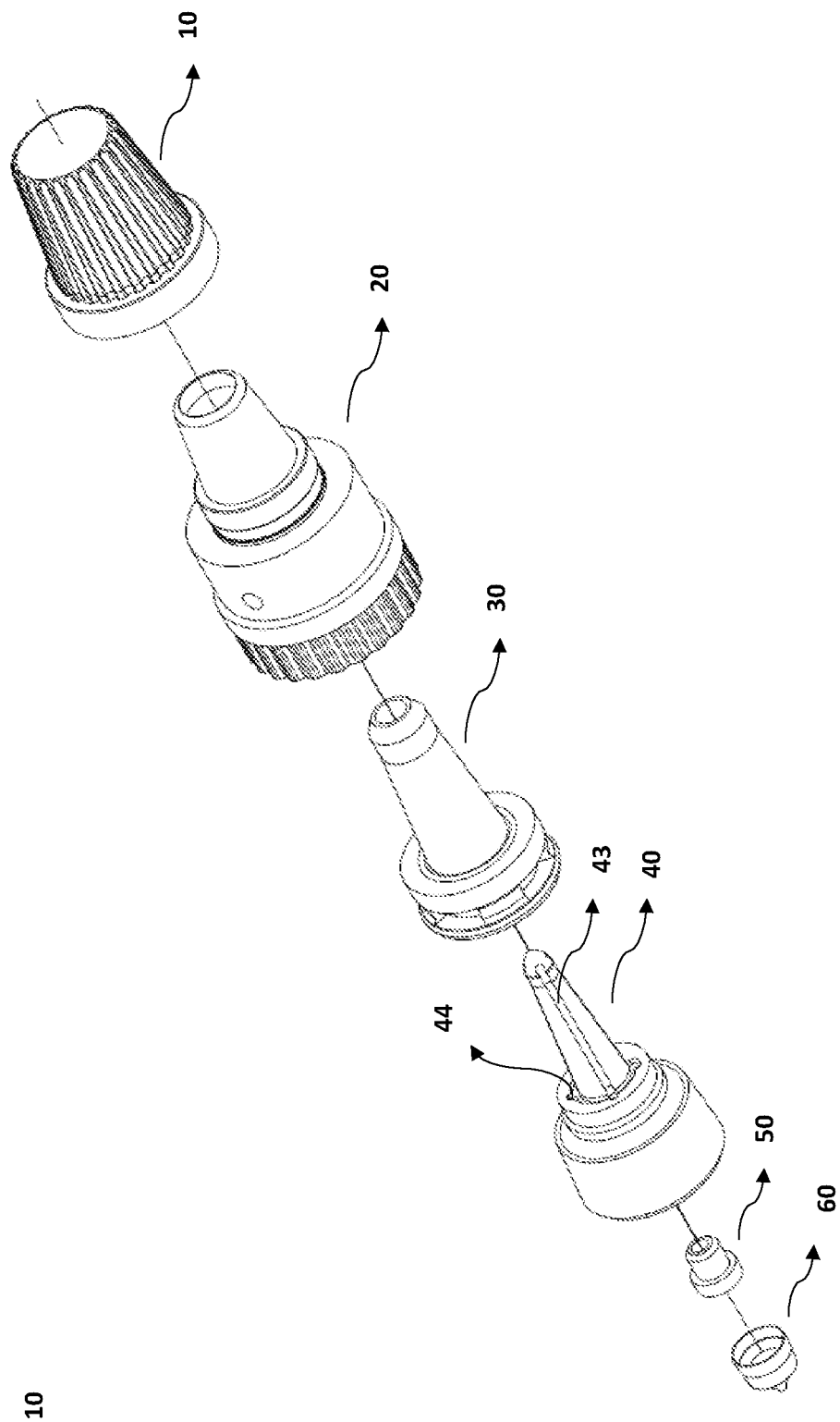
FIG. 1: An exploded view of the present invention.
Figure 2:
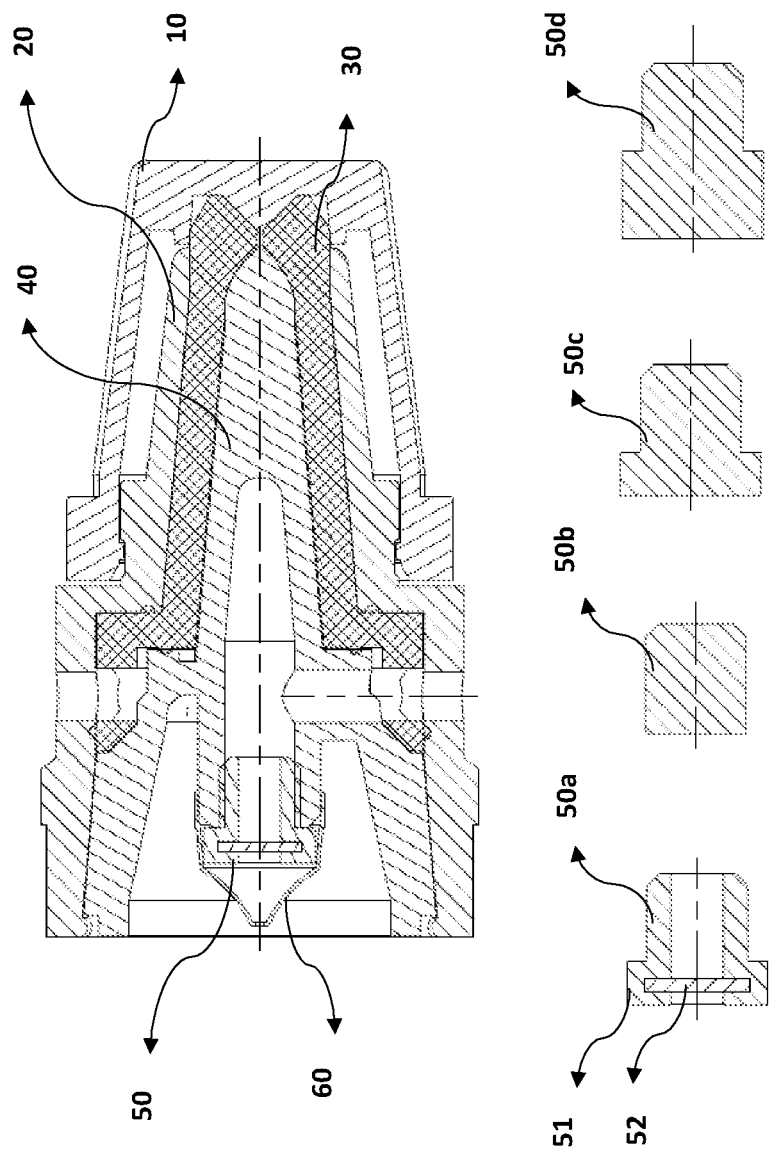
FIG. 2: A cross-sectional view of the present invention is shown with different embodiments of the porous filter.
Figure 3:
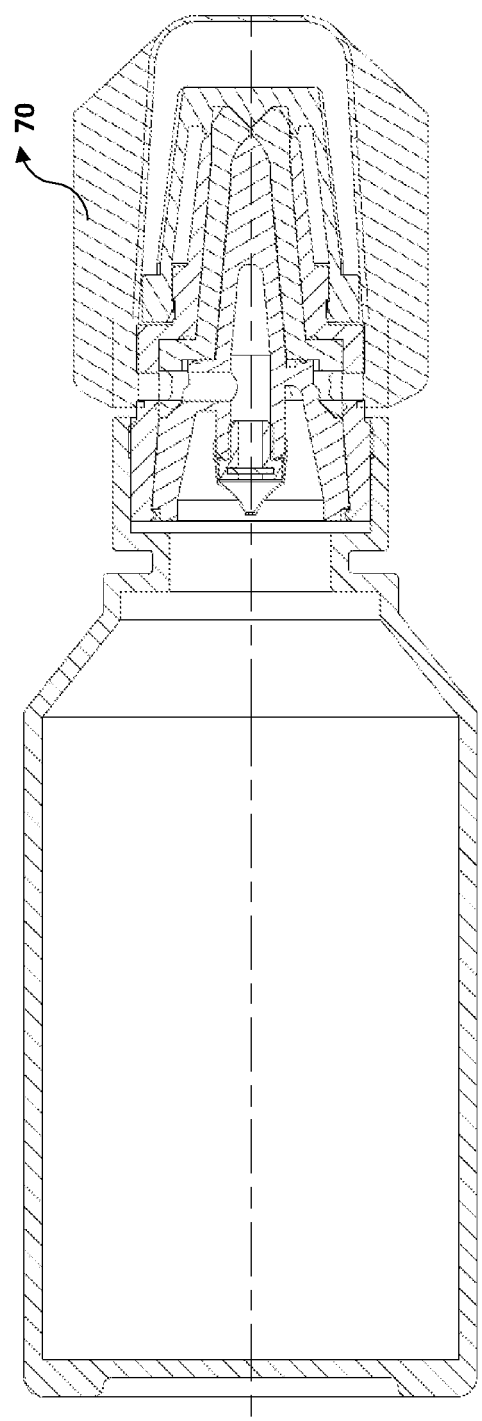
FIG. 3: The present invention is shown arranged in a bottle
Figure 4:
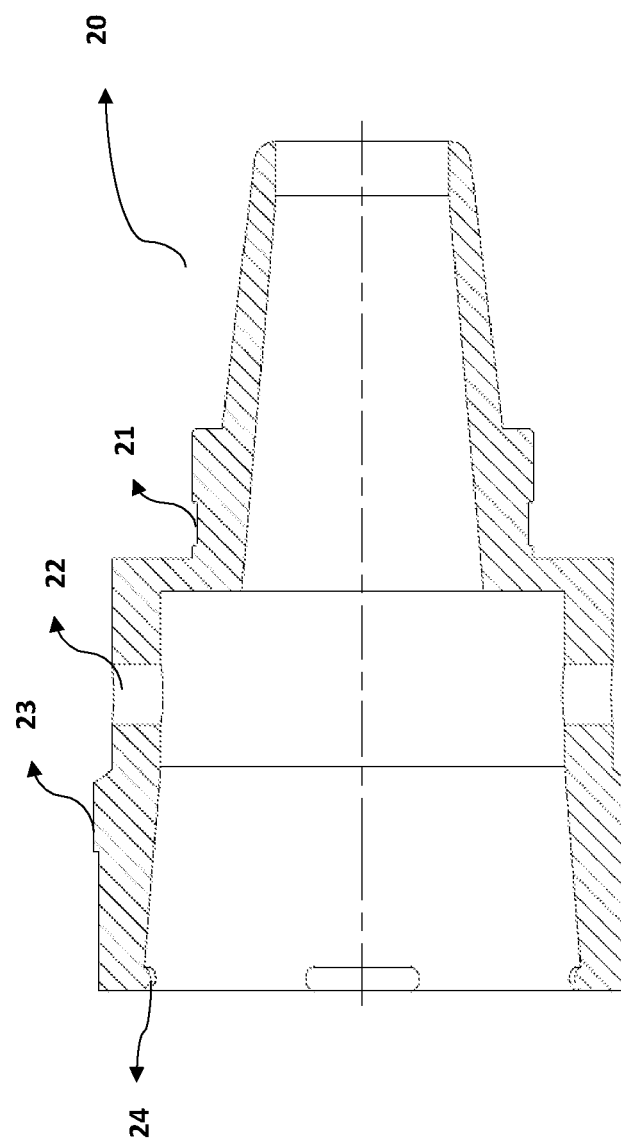
FIG. 4: The upper casing.
Figure 5:
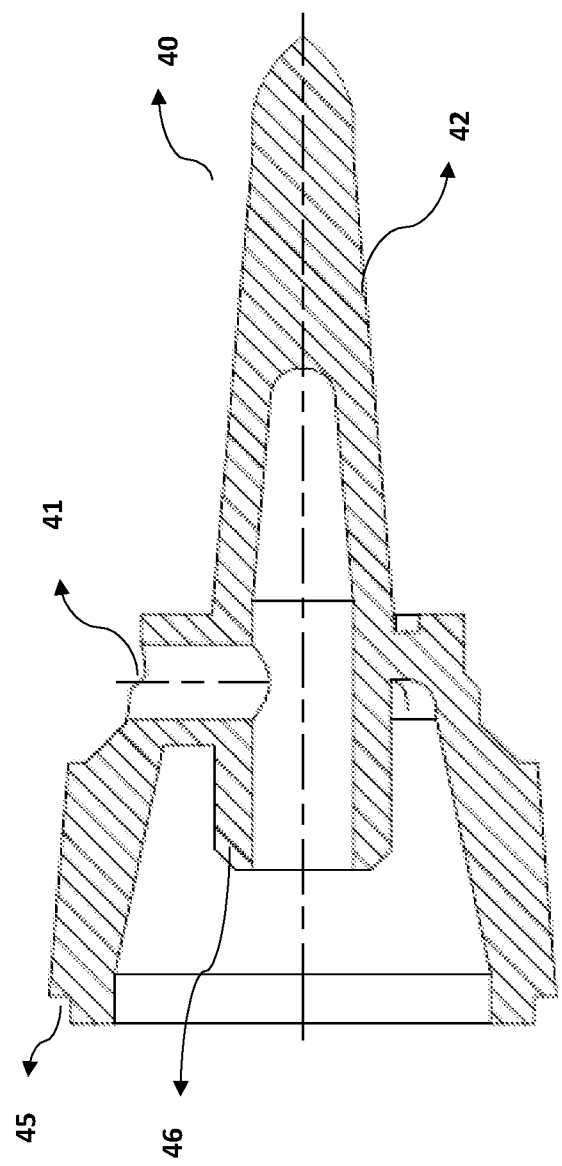
FIG. 5: A first embodiment of the valve holder.
Figure 6:
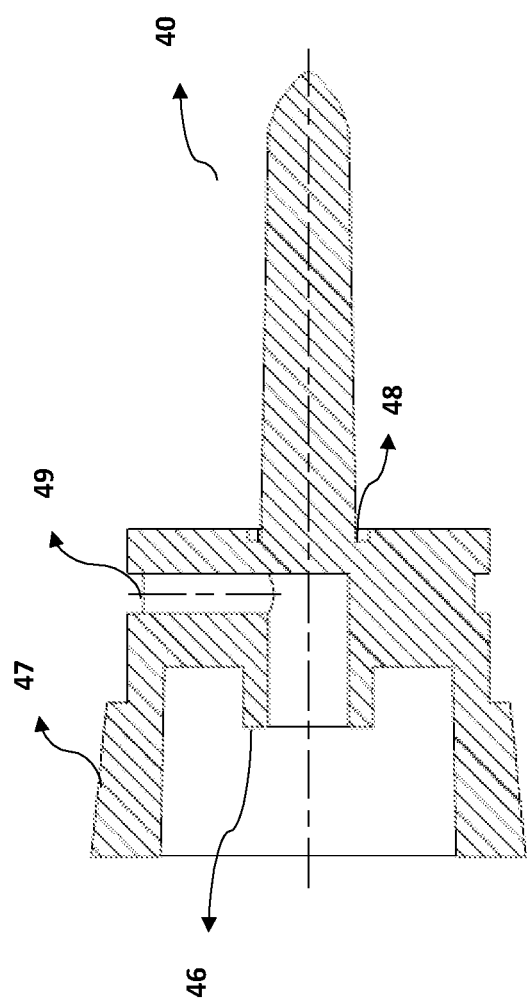
FIG. 6: A second embodiment of the valve holder.
Figure 7:
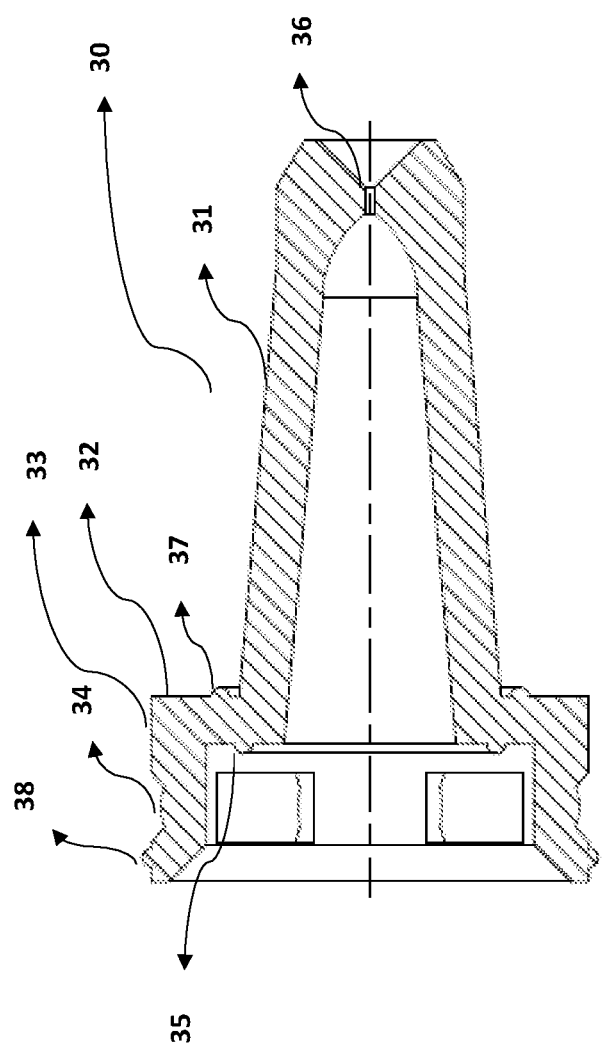
FIG. 7: A cross-sectional view of the membrane valve.
Figure 8:
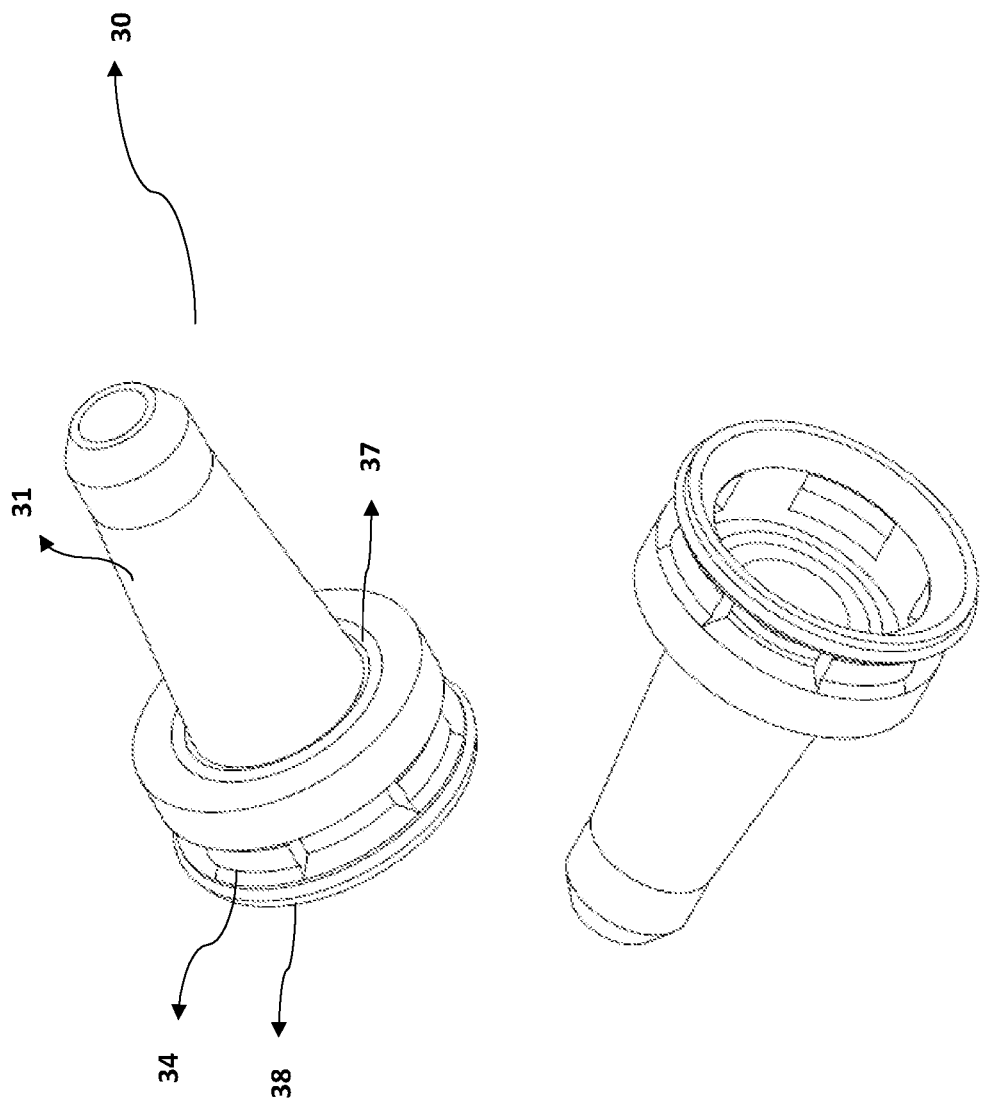
FIG. 8: Two isometric views of the membrane valve.
Figure 9:
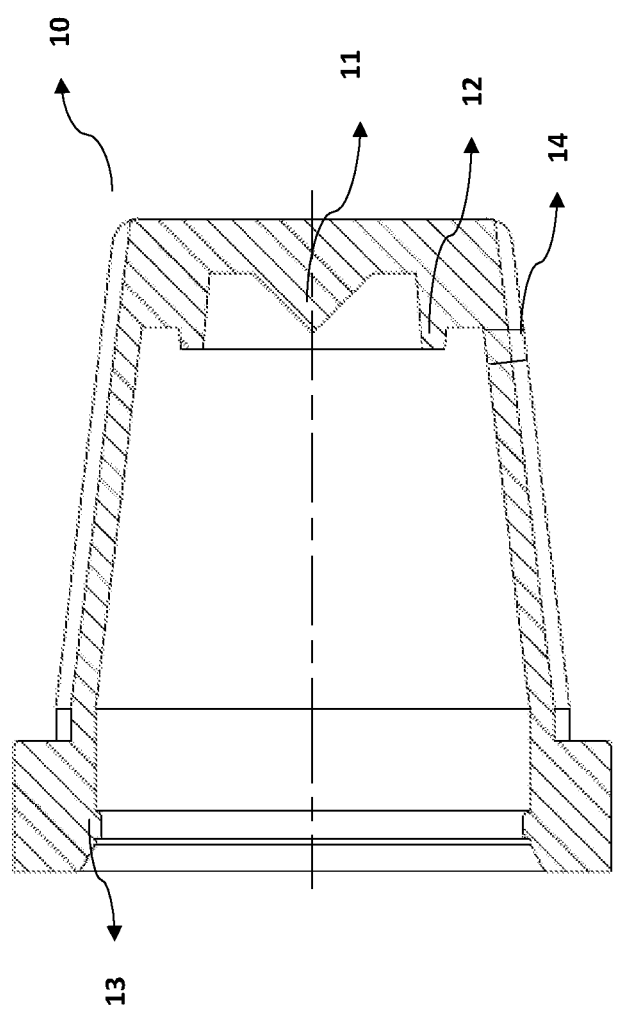
FIG. 9: A cross section of the lid.
Figure 10:
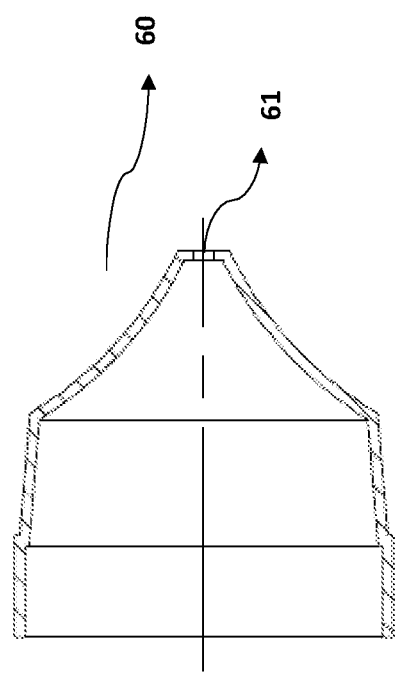
FIG. 10: A porous filter retention device.

The reference numbers included in the figures refer to the following elements:
10: Lid
11: Central protrusion of the cover
12: Guide annular wall
13: Notch in cover
14: Evaporation window
20: Upper casing
21: Depression of the upper casing
22: Side hole disposed at the height of the window
23: Attachment element with drop bottle neck
24: Snap on coupling protrusion
30: Membrane valve
31: Upper part of membrane valve
32: Horizontal or wide extension
33: Vertical extension
34: Windows
35: Annular protrusion on the inner surface of the membrane valve
36: Droplet opening
37: Upper annular protrusion at the beginning of the horizontal extension portion
38: Annular protrusion in the lower end area of the membrane valve
40: Flow circulation body
41: Air compensation through hole
42: Bar or elongated portion
43: Channels
44: Upper through holes
45: Notch at the lower end of the circulation body
46: Internal annular wall of the circulation body
47: Lower sloping portion of the circulation body.
48: Upper annular depression of the circulation body.
49: Annular depression at the level of the membrane valve windows.
50: Filter
50a: Filter with hollow cylinder shape
50b: Solid porous filter
50c: Solid porous filter with external stopper
50d: Large thickness porous solid filter
51: External stopper
52: Filtration membrane
60: Silicone protective cap
61: Narrow hole
70: Protective cap or Seal

DESCRIPTION OF THE PREFERRED EMBODIMENT

The present invention is for use with pharmaceutical liquids of various kinds, but in a preferred embodiment it has been elaborated with ophthalmic liquids in mind, which are conventionally dispensed in dispensers of the type known as tip and cap (Tip & Cap), these dispensers being manufactured mostly by a Blow/Fill/Seal system.

In a preferred form, the solution according with the present invention can also be combined with solutions known from prior state of the art to design its incorporating resistance to bacteria, thus this could include bacteriostatic surfaces that inhibit bacterial growth to eliminate or avoid any impurities which may be introduced.

The membrane valve (30) could be made of polyethylene, a thermoplastic elastomer, polypropylene, or a synthetic polymer, such as silicone.

In a first embodiment, the air compensation through hole (41) of the circulation body includes a filter (50) with walls in the form of a hollow cylinder and an external stopper (51), such filter is suitable to be inserted between some internal cylindrical walls of the flow circulation body (46), notice that between the walls of this filter a flat filtration membrane (52) is located perpendicular to the air flow. In a second embodiment of the filter, this is a solid porous filter, without stoppers (50b) and a thickness such that through it the air must pass, of between 2 to 3 mm. In a third embodiment, the solid porous filter has an external stopper (50c). In a fourth embodiment, the portion of the filter that has contact with the liquid inside the dispensing device has a silicone liner (50d), of approximately 0.05 mm. From the foregoing, it is understood that the circulation body could comprise an internal annular wall (46) suitable to house one of the different types of filters proposed here. The present invention could comprise a silicone protective cap (60) coupled to the internal annular wall of the circulation body which has the function of protecting the air filter (50a, b, c, and d) from contact with some components of the formula of the liquid inside the bottle, avoiding any such event could alter the structure or performance of the filter (50a, b, c, and d). The passage or return of the air is done through a narrow hole (61) which functions as a drop-check valve that allows air to pass through, but not liquids. The concept of the drop-check valve of the narrow opening (61) is produced due to the self-sealing of the elastic characteristics of the silicone, the narrow hole (61) is made by stretching the piece of silicone (60), drilling it with a fine tool like a needle and then letting it revert to its original shape.

In one preferred embodiment, the lower part of the upper casing is press-fitted to a notch (24) in the lower end of the flow circulation body, aided and secured by counter pressure exerted with the upper annular protrusion (37) of the filtering membrane. In another preferred embodiment, the coupling between the upper casing and the lid is through depressions (21) in the upper casing and notches in the lower edges of the lid (13), all of them always under pressure, or counter pressure with fittings of the "click" type. The circulation body could have an outwardly inclined lower portion (47) to force the opening of the upper casing and subsequent coupling with it.

In another preferred embodiment, the present invention comprises a protective cap (70) that protects the drip system in a more efficient way than the previous ones because it covers and inhibits the exposure of the air intake hole of the upper casing or the upper opening of the cap.

The upper inner part of the lid (10) comprises a central protrusion (11) in order to displace the excess liquid suitable for contacting the drop outlet nozzle of the dispenser, optionally an absorbent body could be attached to it; this central protrusion has at least one evaporation space/hole which allows communication with the outside environment to achieve evaporation of the remaining liquid from a drop after each use, even with the lid placed on the dispenser. In addition, this lid presses the beak of the membrane valve and ensures the airtightness of the system; optionally, a guide annular wall (12) of a width slightly larger than the beak of the membrane valve could be provided, in such a way that the tip of the valve (30) fits inside the guide annular wall of the lid, and thus avoid leaks in case the container, by mistake, is stored upside down and/or a change in atmospheric pressure occurs.

The invention claimed is:

1. A liquid dispensing device with a drop-check mechanism, comprising:
    a flow circulation body (40) with at least one air compensation through hole (41), a valve holder in a form of a rod (42) with channels (43), wherein the valve holder is disposed on an upper surface of the flow circulation body; and upper through holes (44) in the upper surface of the flow circulation body;
    a membrane valve (30) with an upper part (31) covering the valve holder, with a droplet opening (36) at a tip of the valve holder; in a lower part of the membrane valve is disposed a horizontally extending portion (32), and continuously a vertically extending portion (33); wherein the vertically extending portion is below the horizontally extending portion; wherein the vertically extending portion comprises windows (34) for flowing of air into a dispensing device; wherein the vertically extending portion comprises at least one annular protrusion in a lower end area of the membrane valve (38) which allows securing between an upper casing (20) and the flow circulation body; wherein the horizontally extending portion comprises at least one annular protrusion on an inner surface of the membrane valve (35) which prevents leakage of liquid; and wherein the at least on air compensation through hole (41) of the flow circulation body is at a level of the windows of the membrane valve; and
    the upper casing (20) that covers the membrane valve and part of the flow circulation body, where a lower part of the upper casing has a pressure coupling (24) with a lower end of the flow circulation body, the upper casing comprises at least one side hole placed at a level of the windows (22) of the membrane valve.

2. The liquid dispensing device with a drop-check mechanism, according to claim 1, wherein the upper casing comprises a pressure coupling protrusion (24) at a level of a notch at the lower end of the flow circulation body (45).

3. The liquid dispensing device with a drop-check mechanism, according to claim 1, wherein the upper surface of the flow circulation body comprises an annular depression (48) at a height of an annular protrusion of the horizontally extending portion (35).

4. The liquid dispensing device with a drop-check mechanism, according to claim 1, wherein the flow circulation body comprises an annular depression at a height of the windows of the membrane valve (49).

5. The liquid dispensing device with a drop-check mechanism, according to claim 1, wherein: said flow circulation body (40) defines an inside for contacting a liquid and an outside exposed to air; and the at least one air compensation through hole (41) of the circulation body includes a filter (50) which has walls in a shape of a hollow cylinder and a stopper, where the filter is suitable to be inserted within cylindrical walls (46) inside the flow circulation body (40); between the walls of the filter, a flat filtration membrane (52) is disposed perpendicular to air flow; wherein said cylindrical walls (46) of the flow circulation body (40) connect said inside with said outside through the at least one air compensation through hole (41).

6. The liquid dispensing device with a drop-check mechanism, according to claim 1, wherein the at least one air compensation through hole of the circulation body includes a solid porous filter with an external stopper portion (50*c*, 50*d*).

7. The liquid dispensing device with a drop-check mechanism, according to claim 1, further comprising a silicone protective cap (61) being attached to an internal annular wall of the circulation body (46).

8. The liquid dispensing device with a drop-check mechanism, according to claim 1, wherein a lid is placed on the upper casing, wherein an upper inner part of the lid (10) comprises a central protrusion (11) and a guide annular wall (12) where a tip of the membrane valve fits (30).

* * * * *